(12) United States Patent
Rosentreter et al.

(10) Patent No.: US 7,045,631 B2
(45) Date of Patent: May 16, 2006

(54) SUBSTITUTED 2-THIO-3,5-DICYANO-4-PHENYL-6-AMINOPYRIDINES AND THEIR USE AS ADENOSINE RECEPTOR-SELECTIVE LIGANDS

(75) Inventors: Ulrich Rosentreter, Wuppertal (DE); Thomas Kramer, Wuppertal (DE); Mitsuyuki Shimada, Nara (JP); Walter Hubsch, Wuppertal (DE); Nicole Diedrichs, Wuppertal (DE); Thomas Krahn, Hagen (DE); Kerstin Henninger, Wuppertal (DE); Johannes-Peter Stasch, Solingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/484,133

(22) PCT Filed: Jul. 3, 2002

(86) PCT No.: PCT/EP02/07324

§ 371 (c)(1),
(2), (4) Date: Jan. 15, 2004

(87) PCT Pub. No.: WO03/008384

PCT Pub. Date: Jan. 30, 2003

(65) Prior Publication Data

US 2004/0176417 A1    Sep. 9, 2004

(30) Foreign Application Priority Data

Jul. 16, 2001    (DE)    ................. 101 34 481

(51) Int. Cl.
  *C07D 213/62*    (2006.01)
  *C07D 417/12*    (2006.01)
(52) U.S. Cl. .................... 546/261; 546/269.7
(58) Field of Classification Search ............ 546/269.7, 546/271.1, 270.7, 261; 514/335, 342
See application file for complete search history.

(56) References Cited

FOREIGN PATENT DOCUMENTS

CA    2386147    12/2001
WO    0125210    12/2001

OTHER PUBLICATIONS

"Adenosine Uptake Inhibitors", Noji et. al., European J. Pharmacology 495 (2004), pp. 1-16.*
Ca 134:295744, "Substituted 2-thio-3,5--dicyano-4-aryl-6-aminopyridines and the use thereof adenosine receptor ligands", Rosentreter et. al.*
Poulsen, S.-A., and Quinn, R. J., "Adenosine Receptors: New Opportunities for Future Drugs" Bioorganic & Medicinal Chemistry, 6: 619-641 (1998).
Olah, M.E. et al., "Cloning expression, and characterization of the unique bovine A1 adenosine receptor. Studies on the ligand binding site by site-directed mutagenesis," J. Biol. Chem. 267, 10764-10770, (1992).
Klotz, K.N. et al., "Comparative pharmacalogy of human adenosine receptor subtypes—characterization of stably transfected receptors in CHO Cells." Naunyn Schmiedebergs Arch. Pharmacol. 35, 1-9, (1998).
Poulsen, S.A. et al., "Adeonosine Receptors: New Opportunities for Future Drugs". Bioorganic and Medicinal Chem, 6, 619-641, (1998).

* cited by examiner

Primary Examiner—Patricia L. Morris

(57) ABSTRACT

Compounds of the formula (I)

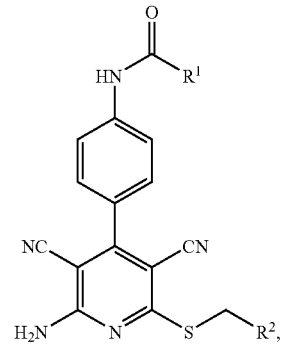

(I)

a process for preparing them, and their use as medicaments are described.

6 Claims, No Drawings

SUBSTITUTED 2-THIO-3, 5-DICYANO-4-PHENYL-6-AMINOPYRIDINES AND THEIR USE AS ADENOSINE RECEPTOR-SELECTIVE LIGANDS

The present invention relates to substituted 2-thio-3,5-dicyano-4-phenyl-6-aminopyridines, to a process for preparing them and to their use as medicaments.

Adenosine, a nucleoside consisting of adenine and D-ribose, is an endogenous factor which exhibits cell-protective activity, in particular under cell-damaging conditions involving restricted oxygen and substrate supply, as occur, for example, in a wide variety of organs (e.g. heart and brain) in association with ischaemia.

While adenosine is formed intracellularly as an intermediate when adenosine-5'-monophosphate (AMP) and S-adenosylhomocysteine are broken down, it can be released from the cell and then exerts functions, by means of binding to specific receptors, as a hormone-like substance or neurotransmitter.

Under normoxic conditions, the concentration of free adenosine in the extracellular space is very low. However, the extracellular concentration of adenosine increases dramatically in the affected organs under ischaemic or hypoxic conditions. Thus, it is known, for example, that adenosine inhibits platelet aggregation and increases the flow of blood through the coronary vessels. In addition, it affects the heart rate, the secretion of neurotransmitters and lymphocyte differentiation.

These effects of adenosine are directed towards increasing the supply of oxygen in the affected organs and/or throttling back the metabolism of these organs in order, in this way, to achieve an adaptation of the organ metabolism to the flow of blood through the organ under ischaemic or hypoxic conditions.

The effect of adenosine is mediated by way of specific receptors. Those which are known to date are the subtypes A1, A2a, A2b and A3. The effects of these adenosine receptors are mediated intracellularly by the messenger compound cAMP. When adenosine binds to the A2a or A2b receptors, the intracellular cAMP is increased as a result of the membrane-located adenylate cyclase being activated, whereas the binding of the adenosine to the A1 or A3 receptors brings about a decrease in the content of intracellular cAMP as a result of the adenylate cyclase being inhibited.

According to the invention, those substances which are able to bind selectively to one or more of the adenosine receptor subtypes and, in this connection, either imitate the effect of adenosine (adenosine agonists) or block its effect (adenosine antagonists) are termed "adenosine receptor-selective ligands".

According to their receptor selectivity, adenosine receptor-selective ligands can be subdivided into various classes, for example into ligands which bind selectively to the A1 or A2 adenosine receptors, and, in the latter case, also, for example, into those which bind selectively to the A2a or A2b adenosine receptors. It is also possible for adenosine receptor ligands to exist which bind selectively to several of the adenosine receptor subtypes, for example ligands which bind selectively to the A1 and A2 adenosine receptors but not to the A3 adenosine receptors.

The abovementioned receptor selectivity can be determined, for example, by the effect of the substances on cell lines which express the relevant receptor subtypes following stable transfection with the appropriate cDNA (in this regard, see the article M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis." in J. Biol. Chem. 267 (1992) pages 10764–10770, the entire disclosure of which is hereby incorporated by reference).

The effect of the substances on such cell lines can be determined by biochemical measurement of the intracellular messenger compound cAMP (in this regard, see the article K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in Naunyn Schmiedebergs Arch. Pharmacol. 357 (1998) pages 1–9, the entire disclosure of which is hereby incorporated by reference).

The adenosine receptor ligands which are disclosed in the prior art are in the main derivatives based on natural adenosine (S.-A. Poulsen and R. J. Quinn, "Adenosine receptors: new opportunities for future drugs" in Bioorganic and Medicinal Chemistry 6 (1998) pages 619–641). However, these adenosine ligands which are known from the prior art usually suffer from the disadvantage that they are less active than the natural adenosine or are only very weakly active, or not active at all, following oral administration. For this reason, they are in the main only used for experimental purposes.

In addition to this, WO 00/125210 discloses 2-thio-3,5-dicyano-4-aryl-6-aminopyridines which are structurally similar to the compounds according to the invention. However, the compounds which are described in the above publication possess disadvantageous pharmacokinetic properties; in particular, they only have low bioavailability following oral administration.

The object of the present invention is now to find or prepare compounds which avoid the disadvantages of the prior art, i.e. which, in particular, possess improved bioavailability.

The present invention relates to compounds of the formula (I)

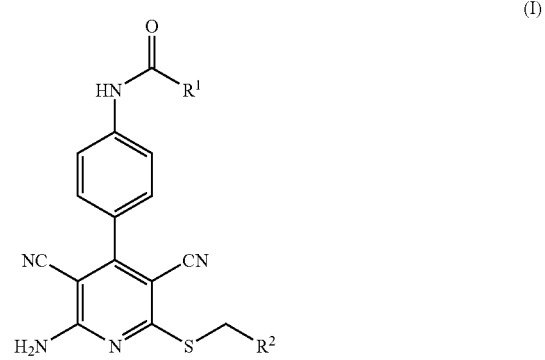

in which
R¹ denotes (C₁–C₄)-alkyl, (C₁–C₄)-alkoxy, or mono- or di-(C₁–C₄)-alkylamino, and
R² denotes pyridyl or thiazolyl, which radicals can be substituted by halogen, amino or (C₁–C₄)-alkyl, and their salts, hydrates, hydrates of the salts and solvates.

Depending on the substitution pattern, the compounds of the formula (I) can exist in stereoisomeric forms which either relate to each other as image and mirror image (enantiomers) or do not relate to each other as image and mirror image (diastereomers). The invention relates both to the enantiomers or diastereomers and to their respective mixtures. The racemic forms can be separated, in a known manner, in exactly the same way as the diastereomers, into the stereoisomerically uniform constituents. Equally, the present invention also relates to the other tautomers of the compounds of the formula (I) and their salts.

Salts of the compounds of the formula (I) can be physiologically harmless salts of the compounds according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, trifluoroacetic acid, acetic acid, propionic acid, lactic acid, tartaric acid, citric acid, fumaric acid, maleic acid or benzoic acid.

Salts which may also be mentioned are salts with customary bases, for example alkali metal salts (e.g. sodium salts or potassium salts), alkaline earth metal salts (e.g. calcium salts or magnesium salts) or ammonium salts which are derived from ammonia or organic amines such as diethylamine, triethylamine, ethyldiisopropylamine, procaine, dibenzylamine, N-methylmorpholine, dihydroabietylamine, 1-ephenamine or methylpiperidine.

According to the invention, those forms of the compounds of the formula (I) which, in the solid or liquid state, form a molecule compound or a complex by hydration with water or coordination with solvent molecules are termed hydrates and solvates, respectively. Examples of hydrates are sesquihydrates, monohydrates, dihydrates and trihydrates. In precisely the same way, the hydrates or solvates of salts of the compounds according to the invention also come into consideration.

In addition, the invention also encompasses prodrugs of the compounds according to the invention. According to the invention, those forms of the compounds of the formula (I) which may themselves be biologically active or inactive but which can be converted (for example metabolically or solvolytically) into the corresponding biologically active form under physiological conditions are termed prodrugs.

Within the context of the present invention, the substituents have, unless otherwise indicated, the following meaning:

Halogen in general represents fluorine, chlorine, bromine or iodine. Fluorine, chlorine or bromine are preferred. Fluorine or chlorine are very particularly preferred.

$(C_1-C_4)$-Alkyl in general represents a straight-chain or branched alkyl radical having from 1 to 4 carbon atoms. Examples which may be mentioned are: methyl, ethyl, n-propyl, isopropyl, n-butyl, sec-butyl, isobutyl and tert-butyl.

$(C_1-C_4)$-Alkoxy in general represents a straight-chain or branched alkoxy radical having from 1 to 4 carbon atoms. Examples which may be mentioned are: methoxy, ethoxy, n-propoxy, isopropoxy, n-butoxy, sec-butoxy, isobutoxy and tert-butoxy.

Mono- or di-$(C_1-C_4)$-alkylamino in general represents an amino group having one or two identical or different straight-chain or branched alkyl substituents which in each case possess from 1 to 4 carbon atoms. Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

Compounds of the formula (I) are preferred in which $R^1$ denotes methyl, ethyl, n-propyl, isopropyl, n-butyl, sec-butyl, isobutyl or tert-butyl, and $R^2$ denotes 2-pyridyl, thiazol-4-yl or thiazol-5-yl, which radicals can be substituted by chlorine, amino or methyl, and their salts, hydrates, hydrates of the salts and solvates.

Particular preference is given to compounds of the formula (I) in which $R^1$ denotes $(C_1-C_4)$-alkyl and their salts, hydrates, hydrates of the salts and solvates.

Particular preference is likewise given to compounds of the formula (I) in which $R^2$ denotes unsubstituted pyridyl and their salts, hydrates, hydrates of the salts and solvates.

Particular preference is likewise given to the compound having the following formula

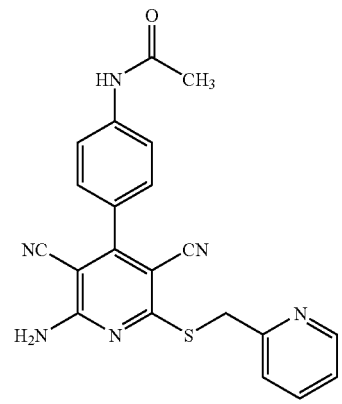

and its salts, hydrates, hydrates of the salts and solvates.

The present invention also relates to a process for preparing the compounds of the formula (I) which is characterized in that compounds of the formula (II)

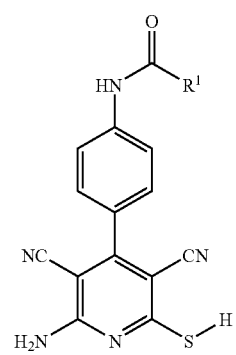

(II)

in which $R^1$ has the abovementioned meaning, are reacted with compounds of the formula (III)

$R^2-CH_2-X$ (III)

in which

R[2] has the abovementioned meaning and X represents a suitable leaving group, preferably halogen, in particular chlorine, bromine or iodine, or represents mesylate, tosylate, triflate or 1-imidazolyl, where appropriate in the presence of a base.

The above-described process can be explained, by way of example, by the following formula scheme:

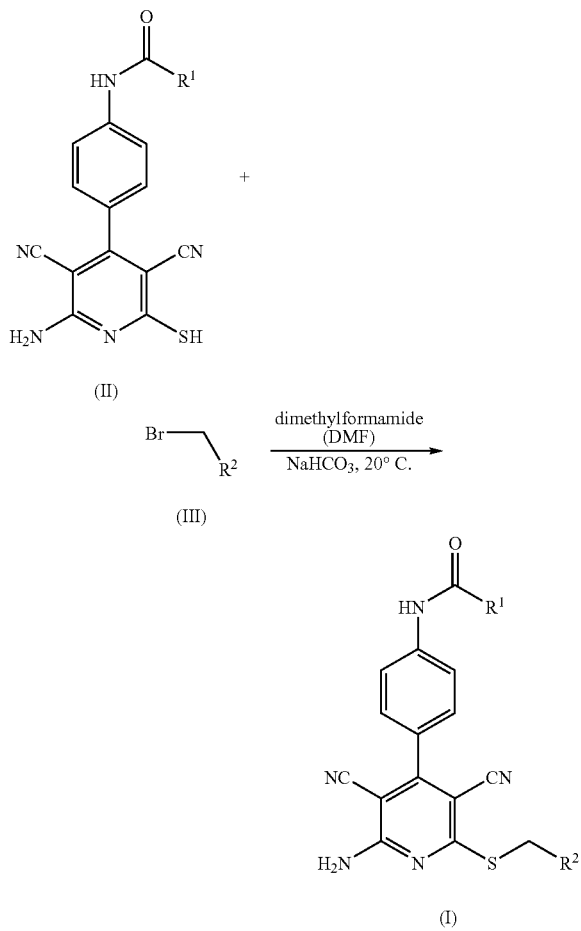

All organic solvents which are inert under the reaction conditions are suitable solvents for the process according to the invention. These solvents include alcohols, such as methanol, ethanol and isopropanol, ketones, such as acetone and methyl ethyl ketone, acyclic and cyclic ethers, such as diethyl ether and tetrahydrofuran, esters such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). Water is likewise suitable for use as a solvent. Dimethylformamide is preferred. It is likewise possible to use mixtures of the abovementioned solvents.

The customary inorganic or organic bases are suitable for use as bases. These bases preferably include alkali metal hydroxides, such as sodium hydroxide or potassium hydroxide, or alkali metal carbonates, such as sodium carbonate or potassium carbonate, or alkali metal hydrogen carbonates, such as sodium hydrogen carbonate or potassium hydrogen carbonate, or alkali metal alkoxides, such as sodium methoxide or potassium methoxide, sodium ethoxide or potassium ethoxide or potassium tert-butoxide, or amides, such as sodium amide, lithium bis(trimethylsilyl)amide or lithium diisopropylamide, or organometallic compounds, such as butyllithium or phenyllithium, or else amines, such as triethylamine and pyridine. The alkali metal carbonates and alkali metal hydrogen carbonates are preferred.

In this connection, the base can be employed in a quantity of from 1 to 10 mol, preferably from 1 to 5 mol, in particular from 1 to 4 mol, based on 1 mole of the compounds of the formula (II).

In general, the reaction takes place in a temperature range from −78° C. up to +140° C., preferably in the range from −78° C. to +40° C., in particular at room temperature.

The reaction can be carried out under normal, increased or decreased pressure (for example in the range from 0.5 to 5 bar). In general, it is carried out under standard pressure.

The compounds of the formula (II) are known to the skilled person or can be prepared using customary methods which are known from the literature.

The compounds of the formula (II) can also be prepared from compounds of the formula (IV) by reacting them with an alkali metal sulphide. This preparation method can be explained, by way of example, by the following formula scheme:

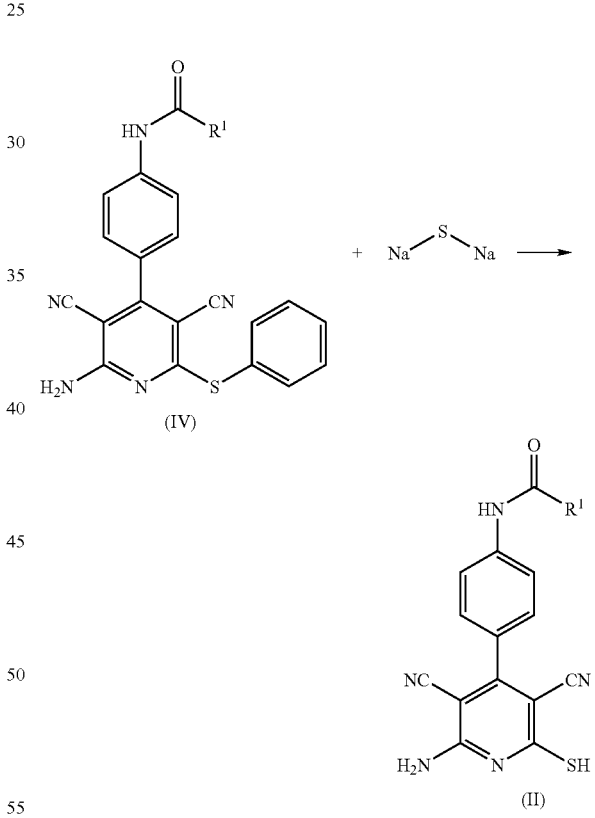

The alkali metal sulphide employed is preferably sodium sulphide, which is employed in a quantity of from 1 to 10 mol, preferably of from 1 to 5 mol, in particular of from 1 to 4 mol, based on 1 mole of the compounds of the formula (IV).

All organic solvents which are inert under reaction conditions are suitable for use as solvents. These include N,N-dimethylformamide, N-methylpyrrolidinone, pyridine and acetonitrile. N,N-Dimethylformamide is particularly preferred. It is likewise possible to use mixtures of the abovementioned solvents.

In general, the reaction takes place in a temperature range from +20° C. to +140° C., preferably in the range from +20° C. to +120° C., in particular at from +60° C. to +100° C.

The reaction can be carried out under normal, increased or decreased pressure (e.g. in the range from 0.5 to 5 bar). In general, it is carried out under standard pressure.

The compounds of the formula (III) are commercially available, or are known to the skilled person or can be prepared using customary methods.

The compounds of the formula (IV) are commercially available, or are known to the skilled person or can be prepared using customary methods. In particular, reference may be made to the following articles, the respective contents of which are hereby incorporated by reference:

Kambe et al., Synthesis, 531–533 (1981);
Elnagdi et al., Z. Naturforsch.47b, 572–578 (1991).

Surprisingly, the compounds of the formula (I) exhibit a valuable pharmacological spectrum of activity, which was not predictable, and are therefore particularly suitable for the prophylaxis and/or treatment of diseases.

As compared with the prior art, the compounds of the formula (I) according to the invention possess superior pharmacokinetic properties, in particular a superior bioavailability following oral administration.

The compounds of the formula (I) are suitable, either alone or in combination with one or more different active compounds, for the prophylaxis and/or treatment of various diseases such as, for example, diseases of the cardiovascular system, in particular. Suitable active compounds for use in combination are, in particular, active compounds for treating coronary heart diseases, for example nitrates, betablockers, calcium antagonists and diuretics, in particular.

Within the meaning of the present invention, cardiovascular diseases are to be understood, for example, as being the following diseases, in particular: coronary heart disease, hypertension (high blood pressure), restenosis, such as restenosis following balloon dilatation of peripheral blood vessels, arteriosclerosis, tachycardias, arrhythmias, peripheral and cardiac vascular diseases, stable and unstable angina pectoris and atrial fibrillation.

The compounds of the formula (I) are furthermore suitable, for example, for reducing the myocardial region affected by an infarction, in particular.

In addition, the compounds of the formula (I) are suitable, for example and in particular, for the prophylaxis and/or treatment of thromboembolic diseases and ischaemias, such as myocardial infarction, cerebral stroke and transitory ischaemic attacks.

Examples of other indication areas for which the compounds of the formula (I) are suitable are, in particular, the prophylaxis and/or treatment of diseases of the urogenital region, such as irritable bladder, erectile dysfunction and female sexual dysfunction, and, in addition, however, also the prophylaxis and/or treatment of inflammatory diseases, such as asthma and inflammatory dermatoses, of neuroinflammatory diseases of the central nervous system, such as conditions occurring after cerebral infarction, and of Alzheimer's disease, and, furthermore, also of neurodegenerative diseases, and also of pain and cancer.

An example of another indication area is, in particular, the prophylaxis and/or treatment of diseases of the airways, such as asthma, chronic bronchitis, pulmonary emphysema, bronchiectases, cystic fibrosis (mucoviscidosis) and pulmonary hypertension.

In addition, the compounds of the formula (I) are also suitable, for example and in particular, for the prophylaxis and/or treatment of liver fibrosis and liver cirrhosis.

Finally, the compounds of the formula (I) are also suitable, for example and in particular, for the prophylaxis and/or treatment of diabetes, in particular diabetes mellitus.

The present invention also relates to the use of the compounds of the formula (I) for producing medicaments for the prophylaxis and/or treatment of the above-mentioned syndromes.

The present invention furthermore relates to a process for the prophylaxis and/or treatment of the abovementioned syndromes using the compounds of the formula (I).

The pharmaceutical activity of the compounds of the formula (I) can be explained by their effects as ligands on adenosine A1 receptors and/or adenosine A2b receptors.

The present invention furthermore relates to medicaments which comprise at least one compound of the formula (I), preferably together with one or more pharmacologically acceptable auxiliary substances or carrier substances, and to their use for the abovementioned purposes.

All the customary administration forms, i.e. that is oral, parenteral, inhalatory, nasal, sublingual, rectal, local, such as in the case of implants or stents, or external, such as transdermal, are suitable for administering the compounds of the formula (I). In the case of parenteral administration, mention may be made, in particular, of intravenous, intramuscular and subcutaneous administration, for example as a subcutaneous depot. Oral or parenteral administration is preferred. Oral administration is particularly preferred.

In this connection, the active compounds can be administered either alone or in the form of preparations. Suitable preparations for oral administration include tablets, capsules, pellets, coated tablets, pills, granules, solid and liquid aerosols, syrups, emulsions, suspensions and solutions. In this connection, the active compound must be present in a quantity which is such that a therapeutic effect is achieved. In general, the active compound can be present in a concentration of from 0.1 to 100% by weight, in particular of from 0.5 to 90% by weight, preferably of from 5 to 80% by weight. In particular, the concentration of the active compound should be 0.5–90% by weight, i.e. the active compound should be present in quantities which are sufficient for achieving the stipulated dosage latitude.

For this purpose, the active compounds can be converted, in a manner known per se, into the customary preparations. This is effected using inert, nontoxic, pharmaceutically suitable carrier substances, auxiliaries, solvents, vehicles, emulsifiers and/or dispersing agents.

Auxiliary substances which may be cited, by way of example, are: water, non-toxic organic solvents, such as paraffins, vegetable oils (e.g. sesame seed oil), alcohols (e.g. ethanol, glycerol), glycols (e.g. polyethylene glycol), solid carrier substances, such as natural or synthetic mineral powders (e.g. talc or silicates), sugars (e.g. lactose), emulsifiers, dispersing agents (e.g. polyvinylpyrrolidone) and glidants (e.g. magnesium sulphate).

In the case of oral administration, tablets can naturally also contain additives, such as sodium citrate, together with admixed substances, such as starch, gelatin and the like. Furthermore, taste improvers or dyes can be added to aqueous preparations for oral administration.

In connection with parenteral administration, it has in general been found to be advantageous, for the purpose of achieving effective results, to administer quantities of from about 0.1 to about 10 000 µg/kg, preferably from about 1 to about 1 000 µg/kg, in particular from about 1 µg/kg to about 100 µg/kg of body weight. In the case of oral administration, the quantity is from about 0.01 to about 10 mg/kg, preferably from about 0.05 to about 5 mg/kg, in particular from about 0.1 to about 1 mg/kg of body weight.

Despite this, it can, where appropriate, be necessary to depart from the abovementioned quantities, depending on the body weight, the route of administration, the individual response to the active compound, the nature of the preparation and the time or interval at which the administration takes place.

The present invention is illustrated by the following, non-limiting, preferred examples, which do not, however, restrict the invention in any way.

Unless otherwise indicated, the percentage values in the following examples in each case refer to the weight; parts are parts by weight.

A. Assessing the Physiological Activity

I. Detecting the Cardiovascular Effect

After the thorax has been opened, the heart is rapidly removed from anaesthetized rats and introduced into a conventional Langendorff apparatus. The coronary arteries are perfused at constant volume (10 ml/min) and the perfusion pressure which arises in this connection is recorded by way of an appropriate pressure sensor. A decrease in the perfusion pressure in this set-up corresponds to a relaxation of the coronary arteries. At the same time, the pressure which the heart develops during each contraction is measured by way of a balloon, which has been introduced into the left ventricle, and a second pressure sensor. The frequency of the heart, which is beating in isolation, is calculated from the number of contractions per unit time.

II. Determining the Adenosine A1, A2a, A2b and A3 Agonism a) Determining the Adenosine Agonism Indirectly by Way of Gene Expression Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of Gi proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance test screening:

The stock cultures are grown, at 37° C. and under 5% $CO_2$, in DMEM/F12 medium containing 10% FCS (foetal calf serum) and in each case split 1:10 after 2–3 days. The test cultures are seeded in 384-well plates at the rate of from 1 000 to 3 000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride $6H_2O$, 5 mM $NaHCO_3$, pH 7.4). The substances, which are dissolved in DMSO, are deleted 1:10 three times with this physiological sodium chloride solution and pipetted into the test cultures (maximum final concentration of DMSO in the test mixture: 0.5%). In this way, final substance concentrations of, for example, from 5 µM to 5 nM are obtained. 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, the plates are shaken for approx. 1 minute and the luciferase activity is measured using a camera system. The adenosine-analogous compound NECA (5-N-ethylcarboxamido-adenosine), which binds to all adenosine receptor subtypes with high affinity and possesses an agonistic effect, is used in these experiments as the reference compound (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1–9).

The following Table 1 gives the values which were obtained for the stimulation of different adenosine receptor subtypes by different concentrations of the compound from Example 1.

TABLE 1

Stimulation of adenosine receptors by different concentrations of the compound from Example 1

| Receptor subtype | Concentration of the compound from Example 1 | | |
|---|---|---|---|
| | 10 nmol | 1 nmol | 0.3 nmol |
| A1 | 5 | 9 | 44 |
| A2a | 57 | 24 | 1 |
| A2b | 88 | 64 | 29 |

The table gives the % values of the corresponding reference stimulus. The measured values for the A2a and A2b receptors are values in percent of the maximum stimulation achieved by NECA; the measured values for the A1 receptor are values in percent following direct prestimulation of the adenylate cyclase with 1µ molar forskolin (corresponds to the 100% value). A1 agonists accordingly exhibit a decrease in the activity of the luciferase (measured value less than 100%).

b) Determining the Adenosine Agonism Directly by way of Detecting cAMP

Cells of the CHO (Chinese Hamster Ovary) permanent cell line are transfected stably with the cDNA for the adenosine receptor subtypes A1, A2a, A2b and A3. The binding of the substances to the A2a or A2b receptor subtypes is determined by measuring the intracellular cAMP content in these cells using a conventional radioimmunological assay (cAMP RIA, IBL GmbH, Hamburg, Germany).

When the substances act as agonists, the binding of the substances is expressed as an increase in the intracellular content of cAMP. The adenosine-analogous compound NECA (5-N-ethylcarboxamido-adenosine), which binds all adenosine receptor subtypes with high affinity and possesses an agonistic effect, is used as the reference compound in these experiments (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1–9).

The adenosine receptors A1 and A3 are coupled to a Gi protein, i.e. stimulation of these receptors leads to inhibition of the adenylate cyclase and consequently to a lowering of the intracellular cAMP level. In order to identify A1/A3 receptor agonists, the adenylate cyclase is stimulated with forskolin. However, an additional stimulation of the A1/A3 receptors inhibits the adenylate cyclase, which means that A1/A3 receptor agonists can be detected by a comparatively low content of cAMP in the cell.

In order to detect an antagonistic effect on adenosine receptors, the recombinant cells which are transfected with the corresponding receptor are prestimulated with NECA and the effect of the substances on reducing the intracellular content of cAMP occasioned by this prestimulation is investigated. XAC (xanthine amine congener), which binds to all adenosine receptor subtypes with high affinity and possesses an antagonistic effect, is used as the reference compound in these experiments (Müller, C. E., Stein, B., Adenosine receptor antagonists: structures and potential therapeutic applications, Current Pharmaceutical Design, 2 (1996) 501–530).

III. Pharmacokinetic Investigations

Pharmacokinetic data were determined after administering various substances i.v. or p.o. as solutions to mice, rats and dogs. For this, blood samples were collected up to 24 hours after administration. The concentrations of the unaltered substance were determined by bioanalytical methods (HPLC or HPLC-MS) in the plasma samples which were obtained from the blood samples. Pharmacokinetic parameters were subsequently ascertained from the plasma concentration time courses which had been obtained in this way. The following Table 2 gives the bioavailability in the different species.

TABLE 2

Bioavailabilities following oral administration

|  | Mouse | Rat | Dog |
| --- | --- | --- | --- |
| Compound from Example 22 in WO 00/125210 | not possible to determine* (at 3 mg/kg p.o.) | not possible to determine* (at 10 mg/kg p.o.) | 1.47% (at 1 mg/ kg p.o.) |
| Compound from Example 1 | 22.1% (at 1 mg/kg p.o.) | 4.6% (at 1 mg/kg p.o.) | 48.2% (at 1 mg/ kg p.o.) |

*Plasma levels at all measurement time points were below the determination limit (<1 μg/l)

B. Implementation Examples

EXAMPLE 1

N-(4-{2-Amino-3,5-dicyano-6-[(2-pyridinylmethyl)sulphanyl]-4-pyridinyl}-phenyl)acetamide 1st Step:

N-[4-(2,2-Dicyanovinyl)phenyl]acetamide

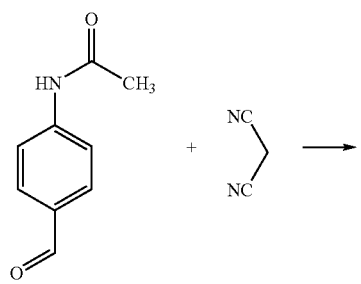

311.4 g (1.9 mol) of 4-acetaminobenzaldehyde and 131 g (1.99 mol) of malonitrile are initially introduced in 1 330 ml of ethanol, and 6 ml of piperidine are then added. The mixture is stirred under reflux for 30 minutes. After cooling down to room temperature, the crystals are filtered off with suction and dried.

Yield: 318 g (79% of theory) Mass spectrum: sought-after relative molar mass: 211; found $[M+H]^+=212$ 2nd Step:

N-{4-[2-Amino-3,5-dicyano-6-(phenylsulphanyl)-4-pyridinyl]phenyl}acetamide

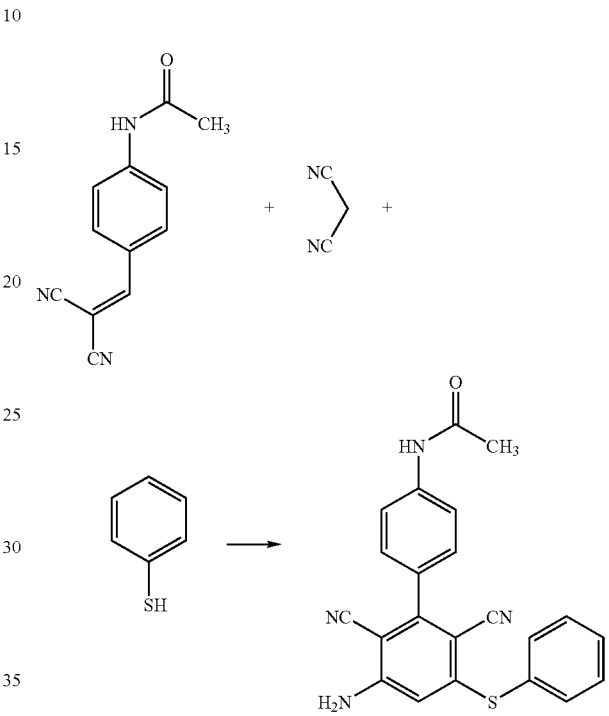

318 g (1.5 mol) of N-[4-(2,2-dicyanovinyl)phenyl]acetamide, 99 g (1.5 mol) of malonitrile and 166 g (1.5 mol) of thiophenol are initially introduced in 2 000 ml of ethanol, and 6.7 ml of triethylamine are then added. The mixture is stirred under reflux for 2 hours, in connection with which crystallization takes place. After the mixture has cooled down to room temperature, the product is filtered off with suction and dried in vacuo.

Yield: 170.3 g (29% of theory) Mass spectrum: sought-after relative molar mass: 385; found $[M+H]^+=386$ 3rd Step:

N-[4-(2-Amino-3,5-dicyano-6-sulphanyl-4-pyridinyl)phenyl]acetamide

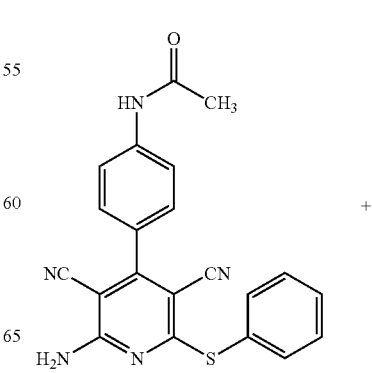

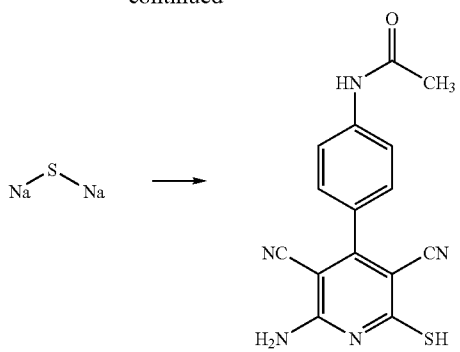

30.83 g (80 mmol) of N-{4-[2-amino-3,5-dicyano-6-(phenylsulphanyl)-4-pyridinyl]-phenyl}-acetamide are dissolved in 120 ml of DMF under argon, after which 9.36 g (120 mmol) of sodium sulphide are added and the mixture is stirred at 80° C. for 2 hours. A solution of 20 ml of 1N aqueous HCl in 44 ml of water is then added dropwise at from 40 to 65° C., after which the crystals which have formed during this procedure are filtered off with suction and washed with water. The precipitate is suspended in 200 ml of methanol and stirred under reflux for 5 minutes. After cooling down to room temperature, the precipitate is filtered off with suction, washed with methanol and diethyl ether and dried in vacuo.

Yield: 24.5 g (88% of theory) Mass spectrum: sought-after relative molar mass: 309; found $[M+H]^+=310.1$ 4th Step:

N-(4-{2-Amino-3,5-dicyano-6-[(2-pyridinylmethyl)sulphanyl]-4-pyridinyl}-phenyl)acetamide

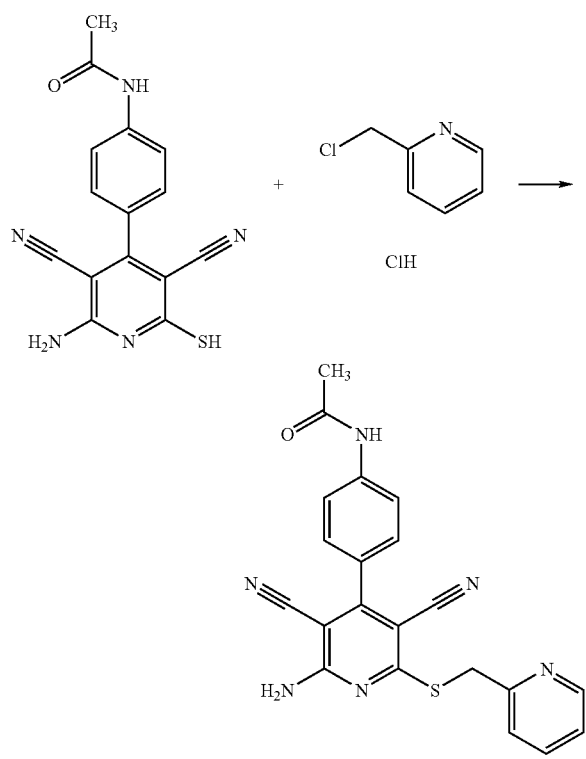

9.28 g (30 mmol) of N-[4-(2-amino-3,5-dicyano-6-sulphanyl-4-pyridinyl)phenyl]-acetamide, 7.38 g (45 mmol) of 2-picolyl chloride hydrochloride and 10.08 g (120 mmol) of sodium hydrogen carbonate are stirred at room temperature in 100 ml of DMF. After 2 hours, 100 ml of water are added dropwise at from 40 to 50° C.

After cooling down to room temperature, the yellow-orange crystals are filtered off with suction and dried in vacuo.

Yield: 10.42 g (86% of theory) Mass spectrum: sought-after relative molar mass: 400; found $[M+H]^+=401$ $^1$H NMR (300 MHz, DMSO-$d_6$): δ=2.1 (s, 3H), 4.6 s (2H), 7.4 (dd, 1H), 7.45 (d, 1H), 7.65 (d, 2H), 7.75 (m, 3H), 8.1 (s broad, 2H), 8.5 (d, 1H), 10.25 (s, 1H).

EXAMPLE 2

Methyl 4-(2-amino-3,5-dicyano-6-{[(2-methyl-1,3-thiazol-4-yl)methyl]-sulphanyl}-4-pyridinyl)phenyl-carbamate 1st Step:

Methyl 4-(2-amino-3,5-dicyano-6-sulphanyl-4-pyridinyl)phenylcarbamate

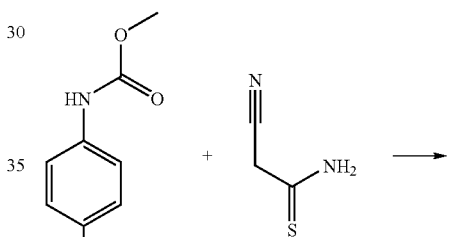

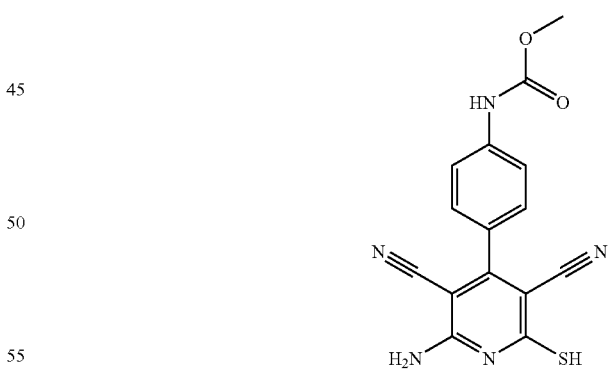

8.5 g (47.4 mmol) of methyl 4-formylphenylcarbamate (Witek et al, Journal f. Prakt. Chemie 321, 804–812 (1979)), 9.5 g (94.9 mmol) of cyanothioacetamide and 9.6 g (94.88 mmol) of N-methylmorpholine are heated under reflux in ethanol for 3 hours. After evaporation, dichloromethane/methanol is added to the residue and the whole is filtered. After having been absorbed to kieselguhr the filtrate is purified by chromatography on silica gel (eluent: dichloromethane/methanol, 100:2 to 100:6). The product fractions are combined and evaporated. The evaporation residue is dissolved in 200 ml of 1N aqueous sodium hydroxide solution and the whole is then filtered. 300 ml of 1N aqueous hydrochloric acid are added to the filtrate and the resulting precipitate is filtered off with suction and dried in vacuo.

Yield: 2.7 g (17% of theory) Mass spectrum: sought-after relative molar mass: 325; found [M+H]$^+$=326 $^1$H NMR (200 MHz, DMSO-d$_6$): δ=3.7 s (3H), 7.4 (d, 2H), 7.6 (d, 2H), 8.1 (s broad, 2H), 10.0 (s, 1H)

2nd Step:

Methyl 4-(2-amino-3,5-dicyano-6-{[(2-methyl-1,3-thiazol-4-yl)methyl]-sulphanyl}-4-pyridinyl)phenylcarbamate

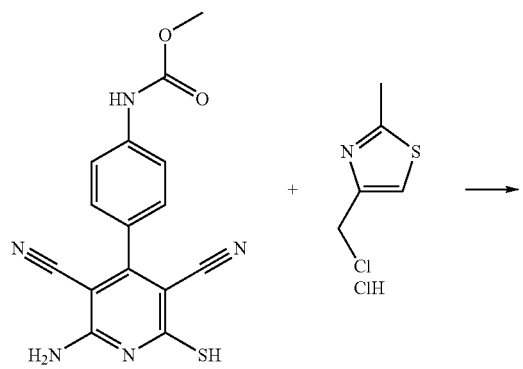

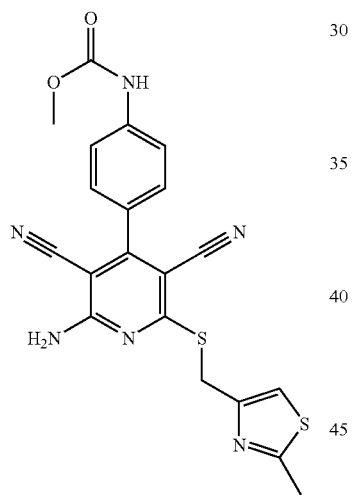

32.5 mg (0.1 mmol) of methyl 4-(2-amino-3,5-dicyano-6-sulphanyl-4-pyridinyl)-phenylcarbamate and 27.6 mg (0.15 mmol) of 4-(chloromethyl)-2-methyl-1,3-thiazole hydrochloride are shaken overnight in 0.4 ml of DMF together with 33.6 mg (0.4 mmol) of sodium hydrogen carbonate. The reaction mixture is filtered and purified by preparative HPLC.

Column: Nucleosil 5C18 Nautilus, 5 μm, 20×50 mm,
Precolumn: Gromsil ODS 4 HE 15 μm 10×20 mm.
Flow rate: 25 ml/min.
Gradient (A=acetonitrile, B=water+0.3% trifluoroacetic acid):

| 0 min | 10% A; |
| 2 min | 10% A; |
| 6 min | 90% A; |
| 7.00 min | 90% A; |
| 7.10 min | 10% A; |
| 8 min | 10% A. |

Detection: 220 nm. Injection volume: 600 μl

The product fraction is evaporated in vacuo.

Yield: 15.8 mg (36% of theory)

Mass spectrum: sought-after relative molar mass: 436; found [M+H]$^+$=437

Abbreviations employed:

| | |
|---|---|
| DMF | Dimethylformamide |
| DMSO | Dimethylsulphoxide |
| HEPES | 2-[4-(2-Hydroxyethyl)piperazino]ethanesulphonic acid |
| HPLC | High pressure or high performance liquid chromatography |
| NMR | Nuclear magnetic resonance spectroscopy |
| RT | Room temperature |
| Tris | 2-Amino-2-(hydroxymethyl)-1,3-propanediol |

What is claimed is:

1. A compound of the formula (I)

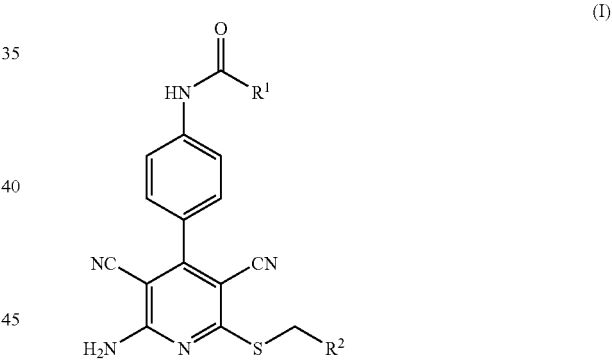

in which

R$^1$ denotes (C$_1$–C$_4$)-alkyl, (C$_1$–C$_4$)-alkoxy, mono- or di-(C$_1$–C$_4$)-alkylamino, and R$^2$ denotes pyridyl or thiazolyl, which radicals can be substituted by halogen, amino or (C$_1$–C$_4$)-alkyl, or a salt, hydrate, or hydrate of the salt thereof.

2. The compound of the formula (I) according to claim 1, in which

R$^1$ denotes methyl, ethyl, n-propyl, isopropyl, n-butyl, sec-butyl, isobutyl or tert-butyl, and R$^2$ denotes 2-pyridyl, thiazol-4-yl or thiazol-5-yl, which radicals can be substituted by chlorine, amino or methyl, or a salt, hydrate, or hydrate of the salt, thereof.

3. The compound according to claim 1 or claim 2 having the following structure

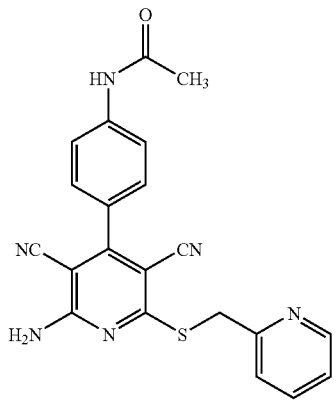

or a salt, hydrate, or hydrate of the salt, thereof.

4. A process for preparing a compound of the formula (I)

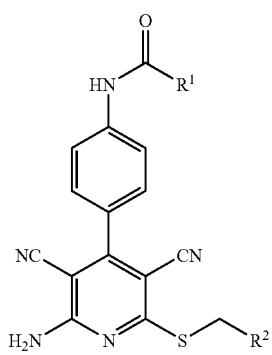

(I)

in which
R$^1$ denotes (C$_1$–C$_4$)-alkyl, (C$_1$–C$_4$)-alkoxy, mono- or di-(C$_1$–C$_4$)-alkylamino, and
R$^2$ denotes pyridyl or thiazolyl, which radicals can be substituted by halogen, amino or (C$_1$–C$_4$)-alkyl,
wherein
a compound of the formula (II)

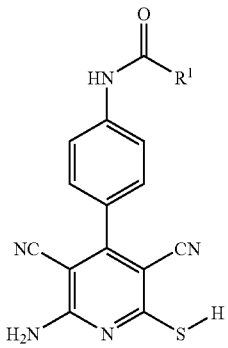

(II)

in which
R$^1$ has the meaning given above,
is reacted with a compound of the formula (III)

$$R^2-CH_2-X \qquad (III)$$

in which
R$^2$ has the meaning given above and X represents a leaving group.

5. A pharmaceutical composition comprising one or more compounds of the formula (I), according to claim 1, and at least one pharmaceutically acceptable carrier.

6. A method for treatment of hypertension comprising administering an effective amount of a compound of claim 1.

* * * * *